United States Patent
Hirota et al.

(10) Patent No.: US 11,710,290 B2
(45) Date of Patent: Jul. 25, 2023

(54) PHOTOACOUSTIC IMAGE EVALUATION APPARATUS, METHOD, AND PROGRAM, AND PHOTOACOUSTIC IMAGE GENERATION APPARATUS

(71) Applicant: FUJIFILM Corporation, Tokyo (JP)

(72) Inventors: Kazuhiro Hirota, Ashigarakami-gun (JP); Kaku Irisawa, Ashigarakami-gun (JP); Dai Murakoshi, Ashigarakami-gun (JP); Yoshiro Imai, Ashigarakami-gun (JP); Tsuyoshi Matsumoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1142 days.

(21) Appl. No.: 16/379,313

(22) Filed: Apr. 9, 2019

(65) Prior Publication Data

US 2019/0231198 A1    Aug. 1, 2019

Related U.S. Application Data

(63) Continuation of application No. PCT/JP2017/030303, filed on Aug. 24, 2017.

(30) Foreign Application Priority Data

Nov. 11, 2016    (JP) .................................. 2016-220110

(51) Int. Cl.
*A61B 5/00*        (2006.01)
*G06V 10/143*      (2022.01)
(Continued)

(52) U.S. Cl.
CPC .......... *G06V 10/143* (2022.01); *A61B 5/0095* (2013.01); *A61B 5/02007* (2013.01);
(Continued)

(58) Field of Classification Search
CPC . A61B 5/0095; A61B 5/02007; A61B 5/7425; A61B 8/06; A61B 8/13;
(Continued)

(56) References Cited

U.S. PATENT DOCUMENTS

| | | | |
|---|---|---|---|
| 2010/0049049 A1 | 2/2010 | Asao et al. | |
| 2011/0144496 A1* | 6/2011 | Li ...................... | A61B 8/0825 600/443 |

(Continued)

FOREIGN PATENT DOCUMENTS

| | | |
|---|---|---|
| CN | 1846645 A | 10/2006 |
| EP | 2 893 868 A1 | 7/2015 |

(Continued)

OTHER PUBLICATIONS

International Preliminary Report on Patentability and Written Opinion of the International Searching Authority (Forms PCT/IB/326, PCT/IB/373, and PCT/ISA/237) for International Application No. PCT/JP2017/030303, dated May 23, 2019, with English translation.

(Continued)

*Primary Examiner* — Joel F Brutus
(74) *Attorney, Agent, or Firm* — Birch, Stewart, Kolasch & Birch, LLP

(57) ABSTRACT

A photoacoustic image evaluation apparatus includes a processor configured to acquire a first photoacoustic image generated at a first point in time and a second photoacoustic image generated at a second point in time before the first point in time, the first and second photoacoustic images being photoacoustic images generated by detecting photoacoustic waves generated inside a subject, who has been subjected to blood vessel regeneration treatment, by emission of light into the subject; acquire a blood vessel regeneration index, which indicates a state of a blood vessel by the regeneration treatment, based on a difference between a (Continued)

blood vessel included in the first photoacoustic image and a blood vessel included in the second photoacoustic image; and display the blood vessel regeneration index on a display.

30 Claims, 9 Drawing Sheets

(51) Int. Cl.
| | |
|---|---|
| *A61B 5/02* | (2006.01) |
| *G06T 7/00* | (2017.01) |
| *G06T 7/33* | (2017.01) |
| *G06T 7/11* | (2017.01) |
| *G01N 29/24* | (2006.01) |
| *G06T 7/149* | (2017.01) |
| *A61B 8/13* | (2006.01) |
| *A61B 8/06* | (2006.01) |
| *G06F 18/22* | (2023.01) |
| *G06V 10/74* | (2022.01) |
| *G06V 40/14* | (2022.01) |

(52) U.S. Cl.
CPC .............. *A61B 5/7425* (2013.01); *A61B 8/06* (2013.01); *A61B 8/13* (2013.01); *G01N 29/2418* (2013.01); *G06F 18/22* (2023.01); *G06T 7/0016* (2013.01); *G06T 7/11* (2017.01); *G06T 7/149* (2017.01); *G06T 7/337* (2017.01); *G06V 10/761* (2022.01); *G01N 2291/02466* (2013.01); *G06T 2207/10132* (2013.01); *G06T 2207/20024* (2013.01); *G06T 2207/20221* (2013.01); *G06V 40/14* (2022.01); *G06V 2201/03* (2022.01); *G06V 2201/031* (2022.01)

(58) Field of Classification Search
CPC . G06F 18/22; G06T 7/11; G06T 7/149; G06T 7/0016
See application file for complete search history.

(56) References Cited

U.S. PATENT DOCUMENTS

| | | |
|---|---|---|
| 2015/0201135 A1 | 7/2015 | Oh et al. |
| 2015/0334308 A1 | 11/2015 | Abe et al. |
| 2018/0322630 A1 | 11/2018 | Stavros et al. |

FOREIGN PATENT DOCUMENTS

| | | |
|---|---|---|
| JP | 2010-46215 A | 3/2010 |
| JP | 2013-17760 A | 1/2013 |
| JP | 2013-34852 A | 2/2013 |
| JP | 2014-140631 A | 8/2014 |
| JP | 2016-515019 A | 5/2016 |

OTHER PUBLICATIONS

International Search Report (Form PCT/ISA/210) for International Application No. PCT/JP2017/030303, dated Nov. 14, 2017, with English translation.
Extended European Search Report dated Oct. 18, 2019, for European Patent Application No. 17868925.3.
Liangzhong Xiang et al.; Pulse laser integrated photodynamic therapy and photoacoustic imaging; Proceedings of SPIE; vol. 6437; Feb. 7, 2007; p. 64372B.
European Communication pursuant to Article 94(3) EPC for European Application No. 17868925.3, dated Jul. 5, 2022.

* cited by examiner

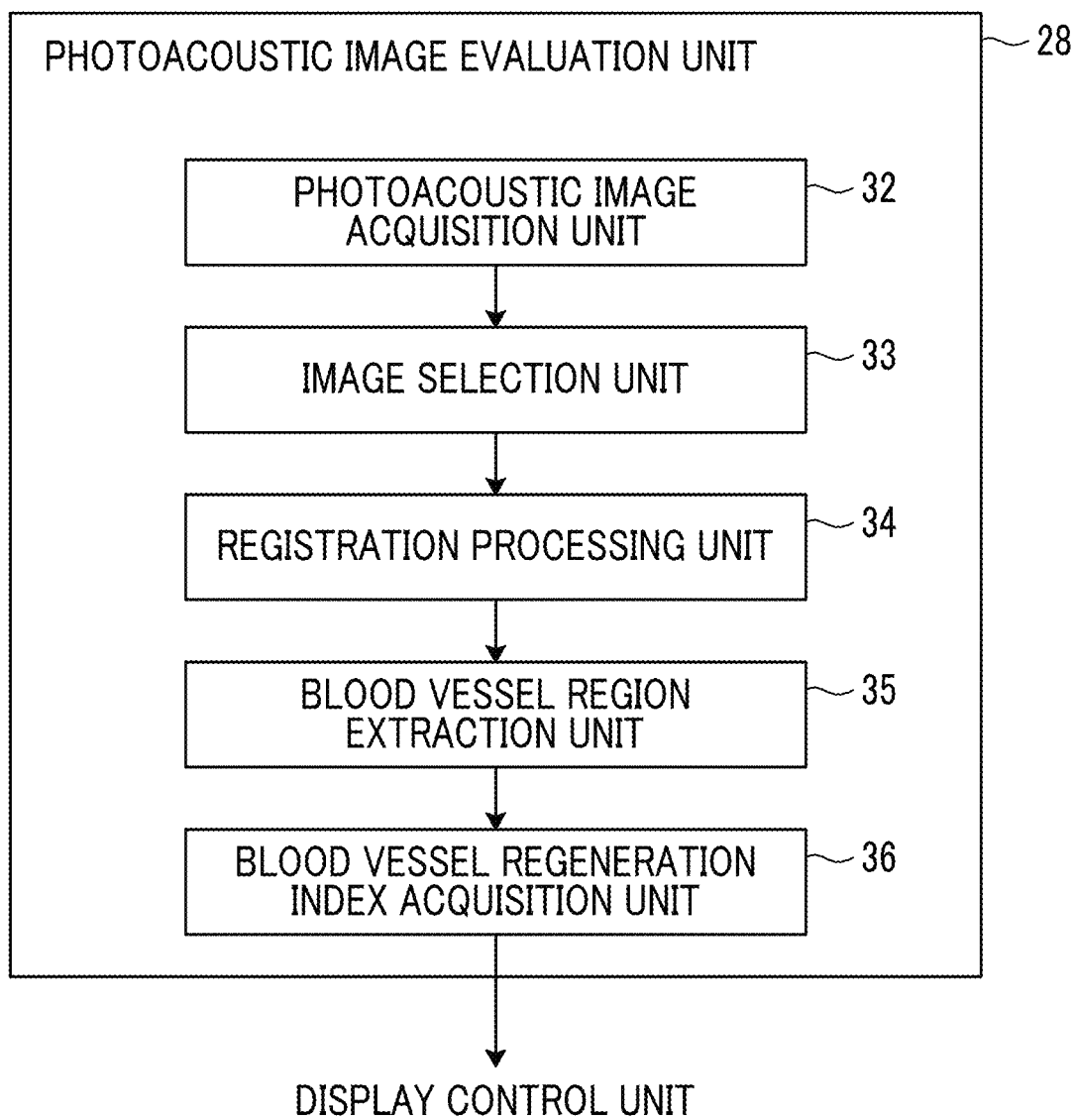

FIG. 11

| INCREASE AMOUNT OF BLOOD VESSEL | RISK |
|---|---|
| ⋮ | ⋮ |
| −10% | 5 |
| −5% | 4 |
| 0% | 3 |
| +5% | 2 |
| +10% | 1 |
| ⋮ | ⋮ |

PHOTOACOUSTIC IMAGE EVALUATION APPARATUS, METHOD, AND PROGRAM, AND PHOTOACOUSTIC IMAGE GENERATION APPARATUS

CROSS-REFERENCE TO RELATED APPLICATIONS

This application is a Continuation of PCT International Application No. PCT/JP2017/030303 filed on Aug. 24, 2017, which claims priority under 35 U.S.C § 119(a) to Japanese Patent Application No. 2016-220110 filed on Nov. 11, 2016. Each of the above application(s) is hereby expressly incorporated by reference, in its entirety, into the present application.

BACKGROUND OF THE INVENTION

1. Field of the Invention

The present invention relates to a photoacoustic image evaluation apparatus, a photoacoustic image evaluation method, a non-transitory computer readable recording medium storing a photoacoustic image evaluation program, and a photoacoustic image generation apparatus for acquiring and displaying a blood vessel regeneration index based on a photoacoustic image generated by detecting photoacoustic waves generated inside a subject, who has been subjected to blood vessel regeneration treatment, by emission of light into the subject.

2. Description of the Related Art

As a kind of image examination method capable of examining the state of the inside of the living body in a non-invasive manner, an ultrasound examination method is known. In ultrasound examination, an ultrasound probe capable of transmitting and receiving ultrasound waves is used. In a case where ultrasound waves are transmitted to a subject (living body) from the ultrasound probe, the ultrasound waves propagate through the living body and are reflected on the tissue interface. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of the living body using the photoacoustic effect is known. In general, in photoacoustic imaging, pulsed laser light is emitted into the living body. Inside the living body, the living tissue absorbs the energy of the pulsed laser light, and ultrasound waves (photoacoustic waves) are generated by adiabatic expansion due to the energy. By detecting the photoacoustic waves using an ultrasound probe or the like and forming a photoacoustic image based on the detection signal, it is possible to visualize the inside of the living body based on the photoacoustic waves (for example, refer to JP2013-034852A and JP2013-017760A).

On the other hand, in recent years, blood vessel regeneration treatment using bone marrow cells has been drawing attention. For example, it is known that bone marrow cells differentiate into blood vessels to cause angiogenesis by directly injecting cells sampled from the bone marrow of lower limbs, in which the blood flow has become worse due to peripheral arterial occlusion, into the lower limbs.

SUMMARY OF THE INVENTION

Here, the regenerated blood vessels generated by the angiogenesis as described above have conventionally been checked by a vascular imaging method using a contrast method (X-ray angiography, angiography computed tomography (CT), angiography magnetic resonance imaging (MRI), and the like).

However, it is difficult to check fine regenerated blood vessels with the vascular imaging method using the contrast method.

Therefore, it is conceivable to check the regenerated blood vessels with a photoacoustic image acquired by the above-described photoacoustic imaging. However, it is difficult to check the effect of regeneration treatment simply by checking the current photoacoustic image.

In view of the aforementioned circumstances, it is an object of the present invention to provide a photoacoustic image evaluation apparatus, a photoacoustic image evaluation method, a non-transitory computer readable recording medium storing a photoacoustic image evaluation program, and a photoacoustic image generation apparatus capable of easily and highly accurately checking the effect of blood vessel regeneration treatment.

A photoacoustic image evaluation apparatus of the present invention comprises: a photoacoustic image acquisition unit that acquires a first photoacoustic image generated at a first point in time and a second photoacoustic image generated at a second point in time before the first point in time, the first and second photoacoustic images being photoacoustic images generated by detecting photoacoustic waves generated inside a subject, who has been subjected to blood vessel regeneration treatment, by emission of light into the subject; a blood vessel regeneration index acquisition unit that acquires a blood vessel regeneration index, which indicates a state of a blood vessel by the regeneration treatment, based on a difference between a blood vessel included in the first photoacoustic image and a blood vessel included in the second photoacoustic image; and a display control unit that displays the blood vessel regeneration index on a display unit.

The photoacoustic image evaluation apparatus of the present invention described above may further comprise: a registration processing unit that performs registration processing between the first photoacoustic image and the second photoacoustic image; and a blood vessel region extraction unit that extracts a first blood vessel region included in the first photoacoustic image and a second blood vessel region included in the second photoacoustic image. In addition, the blood vessel regeneration index acquisition unit may acquire the blood vessel regeneration index based on a difference between the first blood vessel region and the second blood vessel region registered by the registration processing.

In the photoacoustic image evaluation apparatus of the present invention described above, the photoacoustic image acquisition unit may acquire a group of a series of first photoacoustic image candidates consecutively generated at the first point in time. In addition, the photoacoustic image evaluation apparatus of the present invention described above may further comprise an image selection unit that selects the first photoacoustic image, which is to be subjected to the registration processing with the second photoacoustic image, from the group of first photoacoustic image candidates.

In the photoacoustic image evaluation apparatus of the invention described above, the photoacoustic image acquisition unit may acquire a group of a series of second photoacoustic image candidates consecutively generated at the second point in time. In addition, the photoacoustic image evaluation apparatus of the present invention described above may further comprise an image selection unit that selects the second photoacoustic image, which is to be subjected to the registration processing with the first photoacoustic image, from the group of second photoacoustic image candidates.

In the photoacoustic image evaluation apparatus of the present invention described above, the photoacoustic image acquisition unit can acquire a group of a series of first photoacoustic image candidates consecutively generated at the first point in time and a group of a series of second photoacoustic image candidates consecutively generated at the second point in time, and the photoacoustic image evaluation apparatus can further comprise an image selection unit that selects the first photoacoustic image, which is to be subjected to the registration processing with the second photoacoustic image, from the group of first photoacoustic image candidates and selects the second photoacoustic image, which is to be subjected to the registration processing with the first photoacoustic image, from the group of second photoacoustic image candidates.

In the photoacoustic image evaluation apparatus of the invention described above, the image selection unit may select the second photoacoustic image based on an image feature amount of the second photoacoustic image candidate.

In the photoacoustic image evaluation apparatus of the present invention described above, the image selection unit may select the second photoacoustic image candidate, which includes an image of an insert that is inserted into the subject at the time of performing the regeneration treatment, as the second photoacoustic image.

The photoacoustic image evaluation apparatus of the present invention described above may further comprise a past image storage unit that stores the second photoacoustic image, and the past image storage unit may store only the second photoacoustic image selected from the group of second photoacoustic image candidates by the image selection unit.

In the photoacoustic image evaluation apparatus of the present invention described above, the registration processing unit may perform registration processing between the first photoacoustic image and the second photoacoustic image based on some reference regions set in the first photoacoustic image and the second photoacoustic image.

The photoacoustic image evaluation apparatus of the present invention described above may further comprise an ultrasound image acquisition unit that acquires a first ultrasound image corresponding to the first photoacoustic image and a second ultrasound image corresponding to the second photoacoustic image, the first and second ultrasound images being ultrasound images generated by detecting reflected ultrasound waves that are reflected inside the subject by emission of ultrasound waves to the subject. In the photoacoustic image evaluation apparatus of the present invention described above, the registration processing unit may perform registration processing between the first photoacoustic image and the second photoacoustic image based on the first ultrasound image and the second ultrasound image.

In the photoacoustic image evaluation apparatus of the present invention described above, the registration processing unit may perform the registration processing based on a blood vessel having a preset thickness or more.

In the photoacoustic image evaluation apparatus of the present invention described above, the registration processing unit may perform low pass filter processing on the first photoacoustic image and the second photoacoustic image and perform the registration processing on the first photoacoustic image and the second photoacoustic image after the low pass filter processing.

In the photoacoustic image evaluation apparatus of the present invention described above, the blood vessel region extraction unit may extract a region of a blood vessel having the preset thickness or less as the first blood vessel region and the second blood vessel region.

In the photoacoustic image evaluation apparatus of the present invention described above, the blood vessel region extraction unit may extract a region of a blood vessel of 30 µm or more and 300 µm or less as the first blood vessel region and the second blood vessel region.

In the photoacoustic image evaluation apparatus of the present invention described above, the registration processing unit may perform the registration processing by block matching and image deformation processing.

In the photoacoustic image evaluation apparatus of the present invention described above, the blood vessel region extraction unit may perform a plurality of emphasis processing using a plurality of Hessian filters corresponding to a plurality of blood vessel diameters on the first photoacoustic image and the second photoacoustic image, extract the first blood vessel region by integrating blood vessel regions extracted from the first photoacoustic image after the plurality of emphasis processing, and extract the second blood vessel region by integrating blood vessel regions extracted from the second photoacoustic image after the plurality of emphasis processing.

In the photoacoustic image evaluation apparatus of the present invention described above, the blood vessel regeneration index acquisition unit may acquire a regenerated blood vessel region based on the first blood vessel region and the second blood vessel region and acquire the blood vessel regeneration index based on a pattern of a shape of the regenerated blood vessel region.

In the photoacoustic image evaluation apparatus of the present invention described above, the blood vessel regeneration index acquisition unit may specify, as the pattern of the shape of the regenerated blood vessel region, a pattern extending continuously over a preset length or more.

In the photoacoustic image evaluation apparatus of the present invention described above, the blood vessel regeneration index acquisition unit may specify, as the pattern of the shape of the regenerated blood vessel region, a pattern in which a plurality of partial blood vessel regions having a preset length or less are intermittently distributed.

In the photoacoustic image evaluation apparatus of the invention described above, the blood vessel regeneration index acquisition unit may calculate, as the blood vessel regeneration index, a degree of increase of the number of pixels of the first blood vessel region with respect to the number of pixels of the second blood vessel region.

In the photoacoustic image evaluation apparatus of the invention described above, the blood vessel regeneration index acquisition unit may calculate, as the blood vessel regeneration index, a degree of increase of an area of the first blood vessel region with respect to an area of the second blood vessel region.

In the photoacoustic image evaluation apparatus of the invention described above, the display control unit may display the first photoacoustic image and the second photoacoustic image side by side on the display unit.

In the photoacoustic image evaluation apparatus of the invention described above, the first photoacoustic image and the second photoacoustic image may be two-dimensional images.

In the photoacoustic image evaluation apparatus of the invention described above, the first photoacoustic image and the second photoacoustic image may be three-dimensional images.

A photoacoustic image generation apparatus of the present invention comprises: a light emitting unit that emits light to a subject subjected to blood vessel regeneration treatment; a probe having an acoustic wave detection unit that detects photoacoustic waves generated inside the subject by emission of light into the subject; a photoacoustic image generation unit that generates a photoacoustic image based on the photoacoustic waves detected by the acoustic wave detection unit; a photoacoustic image acquisition unit that acquires a first photoacoustic image generated at a first point in time and a second photoacoustic image generated at a second point in time before the first point in time, the first and second photoacoustic images being photoacoustic images generated by the photoacoustic image generation unit; a blood vessel regeneration index acquisition unit that acquires a blood vessel regeneration index, which indicates a state of a blood vessel by the regeneration treatment, based on a difference between a blood vessel included in the first photoacoustic image and a blood vessel included in the second photoacoustic image; and a display control unit that displays the blood vessel regeneration index on a display unit.

In the photoacoustic image generation apparatus of the present invention described above, it is preferable that a wavelength of light emitted from the light emitting unit is 500 nm or more and 1200 nm or less.

In the photoacoustic image generation apparatus of the present invention described above, it is preferable that a center frequency of the probe is 9 MHz or more and 50 MHz or less.

In the photoacoustic image generation apparatus of the present invention described above, it is preferable that the acoustic wave detection unit has a transducer array in which a plurality of transducers are arranged and a pitch between the transducers in the transducer array is 0.05 μm or more and 200 μm or less.

A photoacoustic image evaluation method of the present invention comprises: acquiring a first photoacoustic image generated at a first point in time and a second photoacoustic image generated at a second point in time before the first point in time, the first and second photoacoustic images being photoacoustic images generated by detecting photoacoustic waves generated inside a subject, who has been subjected to blood vessel regeneration treatment, by emission of light into the subject; acquiring a blood vessel regeneration index, which indicates a state of a blood vessel by the regeneration treatment, based on a difference between a blood vessel included in the first photoacoustic image and a blood vessel included in the second photoacoustic image; and displaying the blood vessel regeneration index on a display unit.

A non-transitory computer readable recording medium storing a photoacoustic image evaluation program of the present invention causes a computer to function as: a photoacoustic image acquisition unit that acquires a first photoacoustic image generated at a first point in time and a second photoacoustic image generated at a second point in time before the first point in time, the first and second photoacoustic images being photoacoustic images generated by detecting photoacoustic waves generated inside a subject, who has been subjected to blood vessel regeneration treatment, by emission of light into the subject; a blood vessel regeneration index acquisition unit that acquires a blood vessel regeneration index, which indicates a state of a blood vessel by the regeneration treatment, based on a difference between a blood vessel included in the first photoacoustic image and a blood vessel included in the second photoacoustic image; and a display control unit that displays the blood vessel regeneration index on a display unit.

According to the non-transitory computer readable recording medium storing the photoacoustic image evaluation apparatus, the photoacoustic image evaluation method, the photoacoustic image evaluation program, and the photoacoustic image generation apparatus of the present invention, the first photoacoustic image generated at the first point in time and the second photoacoustic image generated at the second point in time before the first point in time are acquired, the first and second photoacoustic images being photoacoustic images generated by detecting photoacoustic waves generated inside the subject, who has been subjected to blood vessel regeneration treatment, by emission of light into the subject. Then, the blood vessel regeneration index indicating the state of the blood vessel by the regeneration treatment is acquired based on the difference between the blood vessel included in the first photoacoustic image and the blood vessel included in the second photoacoustic image, and the blood vessel regeneration index is displayed on the display unit. Therefore, it is possible to easily and highly accurately check the effect of blood vessel regeneration treatment.

BRIEF DESCRIPTION OF THE DRAWINGS

FIG. 3 is a block diagram showing the schematic configuration of a photoacoustic image evaluation unit.

FIG. 11 is a diagram showing an example of a table in which the increase amount of blood vessel by regeneration treatment and the risk of disease are associated with each other.

DESCRIPTION OF THE PREFERRED EMBODIMENTS

Figure 1:
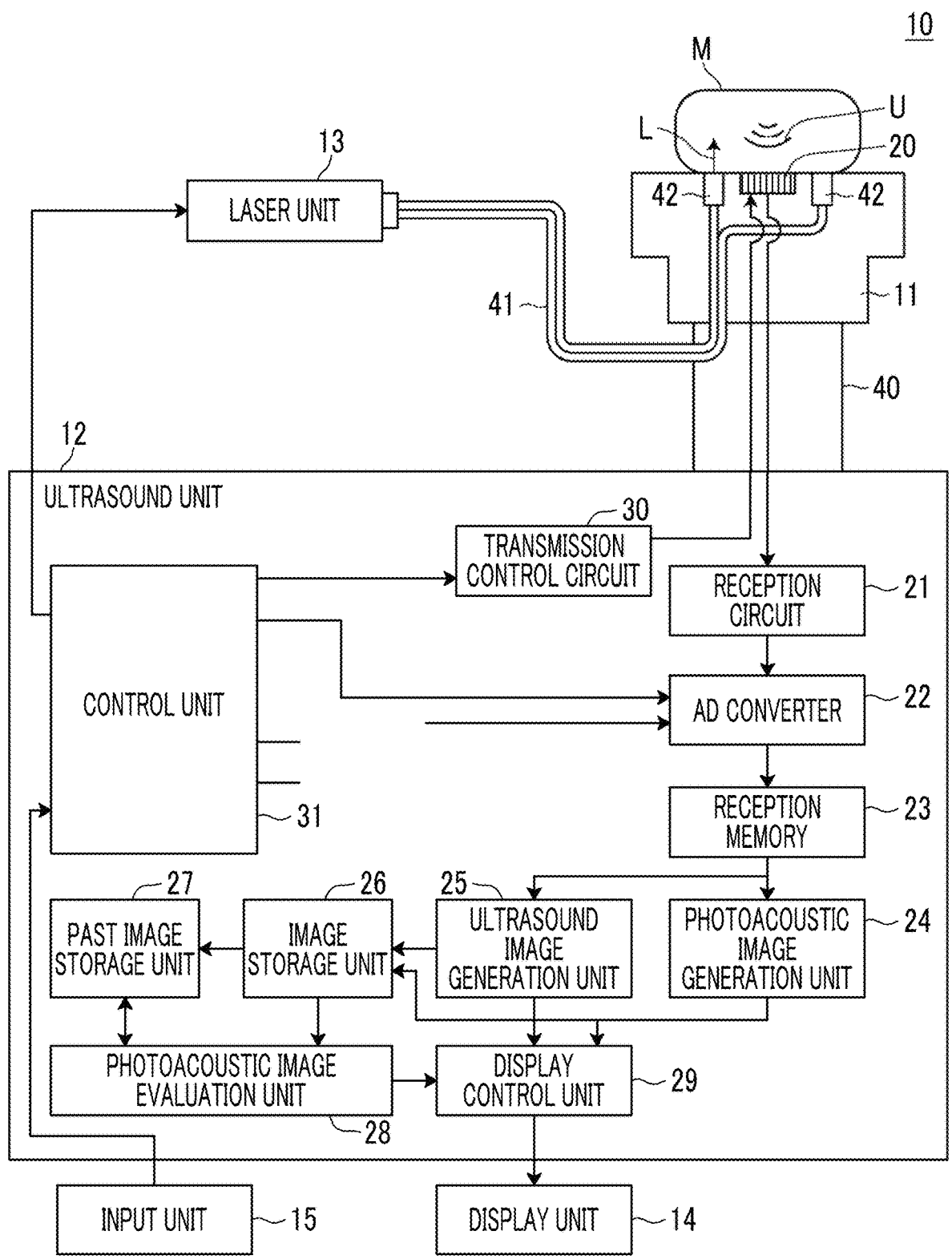
FIG. 1 is a block diagram showing the schematic configuration of a photoacoustic image generation apparatus using an embodiment of a photoacoustic image evaluation apparatus of the present invention.

Hereinafter, a photoacoustic image generation apparatus 10 using an embodiment of a photoacoustic image evaluation apparatus of the present invention will be described in detail with reference to the diagrams. FIG. 1 is a diagram showing the schematic configuration of the photoacoustic image generation apparatus 10 of the present embodiment.

As shown in FIG. 1, the photoacoustic image generation apparatus 10 of the present embodiment comprises an ultrasound probe 11, an ultrasound unit 12, a laser unit 13, a display unit 14, and an input unit 15.

The photoacoustic image generation apparatus 10 of the present embodiment emits laser light to a subject M subjected to blood vessel regeneration treatment and detects a blood vessel inside the subject M by detecting a photoacoustic wave generated by an absorber (for example, hemoglobin) inside the subject M, so that it is possible to check the effect of the regeneration treatment. Hereinafter, the specific configuration of the photoacoustic image generation apparatus 10 will be described.

The ultrasound probe 11 detects a photoacoustic wave U generated inside the subject M and outputs a photoacoustic wave signal. The ultrasound probe 11 transmits ultrasound waves to the subject, detects reflected ultrasound waves from the subject with respect to the transmitted ultrasound waves, and outputs a reflected wave signal.

Here, the "ultrasound wave" means an elastic wave transmitted from the ultrasound probe 11 and its reflected wave, and the "photoacoustic wave" means an elastic wave that is generated inside the subject M by the photoacoustic effect due to emission of measurement light (for example, laser light). In addition, transmission and reception of ultrasound waves may be separated. For example, ultrasound waves may be transmitted from a position different from the ultrasound probe 11, and reflected ultrasound waves of the transmitted ultrasound waves may be received by the ultrasound probe 11.

Figure 2A:
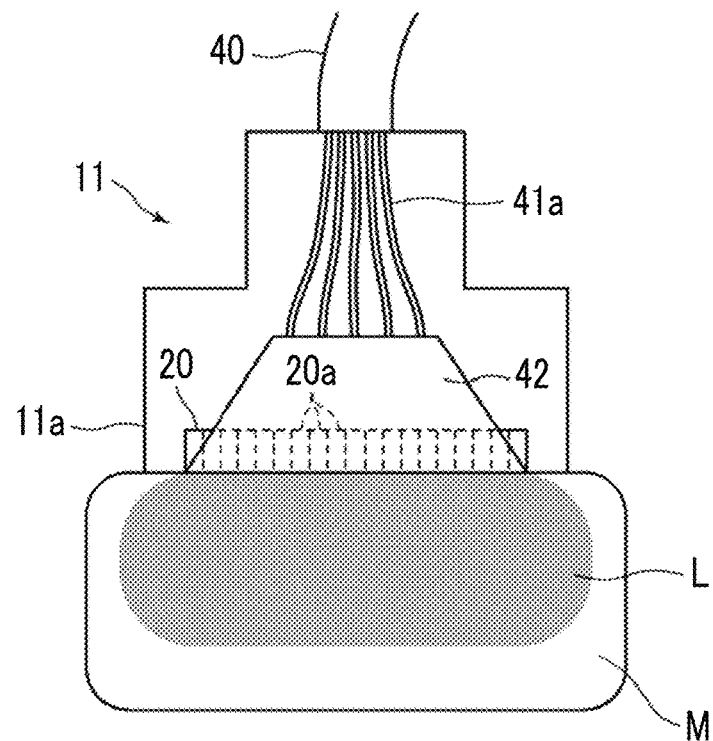
FIG. 2A is a front sectional view of an ultrasound probe.
Figure 2B:
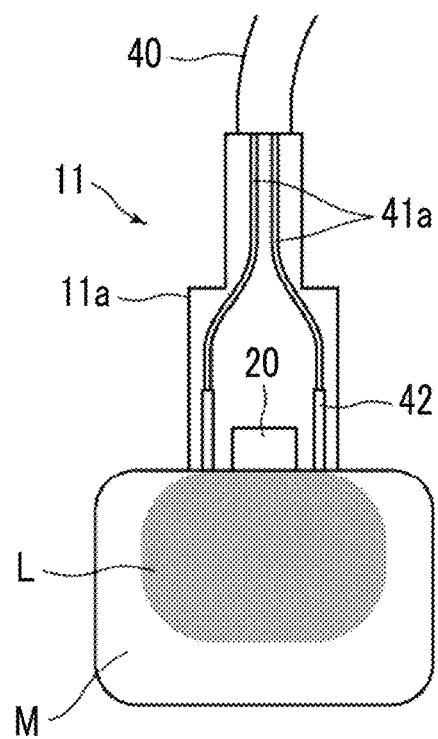
FIG. 2B is a side sectional view of the ultrasound probe.

The ultrasound probe 11 (corresponding to the probe of the present invention) is connected to the ultrasound unit 12 through a cable 40. FIGS. 2A and 2B are schematic configuration diagrams of the ultrasound probe 11. FIG. 2A is a front sectional view of the ultrasound probe 11, and FIG. 2B is a side sectional view of the ultrasound probe 11.

As shown in FIGS. 1, 2A, and 2B, the ultrasound probe 11 comprises a transducer array 20, a bundle fiber 41 in which a plurality of optical fibers 41a are bundled, two light emitting units 42 disposed so as to interpose the transducer array 20 therebetween, and a housing 11a in which these are housed.

The transducer array 20 is configured to include a plurality of ultrasound transducers 20a (or acoustic wave detection elements) arranged in a one-dimensional or two-dimensional manner, for example. In the present embodiment, the ultrasound transducer 20a corresponds to the transducer of the present invention, and the transducer array 20 corresponds to the acoustic wave detection unit of the present invention. The ultrasound transducer 20a is, for example, a piezoelectric element formed of a polymer film, such as piezoelectric ceramics or polyvinylidene fluoride (PVDF). The ultrasound transducer 20a has a function of converting the received signal into an electrical signal in a case where the photoacoustic wave U or the reflected ultrasound wave is received, and the electrical signal generated by the ultrasound transducer is output to a reception circuit 21 to be described later. The ultrasound probe 11 is selected according to an imaging part among a sector type, a linear type, a convex type, and the like.

In the present embodiment, in order to detect fine blood vessels regenerated by regeneration treatment, it is preferable that the pitch between the ultrasound transducers 20a in the transducer array 20 is 0.05 µm or more and 200 µm or less. In addition, it is preferable that the center frequency of the ultrasound probe 11 is 9 MHz or more and 50 MHz or less.

The bundle fiber 41 guides the laser light from the laser unit 13 to the light emitting unit 42. The bundle fiber 41 is not particularly limited, and known fibers, such as a quartz fiber, can be used. The bundle fiber 41 branches for each optical fiber 41a on the emission side, and is connected to the light emitting unit 42.

The light emitting unit 42 is a unit that emits the laser light guided by the bundle fiber 41 to the subject M. As shown in FIGS. 1 and 2B, in the present embodiment, the two light emitting units 42 are disposed on both sides of the transducer array 20 so as to face each other with the transducer array 20 interposed therebetween. As the light emitting unit 42, for example, a light guide plate can be used. The light guide plate is a plate formed by performing special processing on the surface of, for example, an acrylic plate or a quartz plate so that light incident from one end surface is uniformly surface-emitted from the other end surface. In order to uniformly illuminate the subject surface disposed on both sides of the transducer array 20, it is preferable that the width of the transducer array 20 in the array direction and the width of the light guide plate are approximately the same length. In addition, a diffusion plate may be provided at the incidence end or the emission end of the light guide plate.

The laser unit 13 has, for example, a solid state laser light source using a Q switch that emits laser light, and outputs laser light as measurement light L to irradiate the subject M. The laser unit 13 is configured to receive a trigger signal from a control unit 31 of the ultrasound unit 12 and output laser light, for example. It is preferable that the laser unit 13 outputs pulsed light having a pulse width of 1 ns to 100 ns as the laser light. In the present embodiment, the light source of the laser unit 13 is, for example, an alexandrite laser using a Q switch.

The wavelength of laser light is appropriately determined by the light absorption characteristics of an absorber inside a subject as a measurement target. In the present embodiment, since a blood vessel is detected as described above, that is, the measurement target is hemoglobin inside the living body, it is preferable to use a wavelength in the vicinity of the near-infrared wavelength range. More preferably, the wavelength of the laser light is 500 nm to 1200 nm. However, the wavelength of the laser light is not limited thereto. In addition, the laser light may have a single wavelength, or may include a plurality of wavelengths (for example, 750 nm and 800 nm). In a case where the laser light includes a plurality of wavelengths, light beams having these wavelengths may be simultaneously emitted to the subject M, or may be emitted while being switched alternately. In addition to the alexandrite laser, an Nd:YAG laser, a YAG-SHG-OPO laser, and a Ti-Sapphire laser capable of similarly outputting laser light in the near-infrared wavelength range and an SHG-Nd:YAG laser capable of outputting laser light in the visible wavelength range can also be used as the laser unit 13.

The ultrasound unit 12 has the reception circuit 21, an analog to digital convertor (AD converter) 22, a reception memory 23, a photoacoustic image generation unit 24, an ultrasound image generation unit 25, an image storage unit 26, a past image storage unit 27, a photoacoustic image evaluation unit 28, a display control unit 29, a transmission control circuit 30, and the control unit 31. In the present embodiment, the photoacoustic image evaluation unit 28 and the display control unit 29 in the ultrasound unit 12 correspond to the photoacoustic image evaluation apparatus of the present invention.

The ultrasound unit 12 is configured to include, for example, a computer, and typically has a processor, a memory, a bus, and the like. A program relevant to photoacoustic image generation and ultrasound image generation and an embodiment of a photoacoustic image evaluation program of the present invention are installed on the memory of the ultrasound unit 12. By running the programs using the control unit 31 configured by a processor, functions of the photoacoustic image generation unit 24, the ultrasound image generation unit 25, the photoacoustic image evaluation unit 28, and the display control unit 29 are realized. That is, each of these units is formed by the memory on which the programs are installed and the processor.

The configuration of the hardware of the ultrasound unit 12 is not particularly limited, and can be realized by appropriately combining a plurality of integrated circuits (ICs), processors, application specific integrated circuits (ASICs), field-programmable gate arrays (FPGAs), memories, and the like.

The reception circuit 21 receives the photoacoustic wave signal and the reflected wave signal output from the ultrasound probe 11. Typically, the reception circuit 21 includes a low noise amplifier, a variable gain amplifier, and a low pass filter. The photoacoustic wave signal and the reflected wave signal output from the ultrasound probe 11 are amplified by the low noise amplifier, and then the gain is adjusted according to the depth by the variable gain amplifier and high frequency components are cut by the low pass filter.

The AD converter 22 converts the photoacoustic wave signal and the reflected wave signal received by the reception circuit 21 into digital signals. The AD converter 22 samples the photoacoustic wave signal and the reflected wave signal at predetermined sampling periods based on, for example, a sampling clock signal having a predetermined period. The AD converter 22 stores the sampled photoacoustic wave signal and reflected wave signal (sampling data) in the reception memory 23. The reception circuit 21 and the AD converter 22 may be formed as one IC or may be formed as individual ICs, for example.

The photoacoustic image generation unit 24 generates a photoacoustic image based on the photoacoustic wave signal stored in the reception memory 23. The generation of a photoacoustic image includes, for example, image reconstruction such as a Fourier transfer algorithm (FTA) method or a delayed addition (phase matching addition) method, detection, and logarithmic conversion.

The ultrasound image generation unit 25 generates an ultrasound image based on the reflected wave signal stored in the reception memory 23. The generation of an ultrasound image also includes image reconstruction such as phase matching addition, detection, and logarithmic conversion.

The control unit 31 controls each unit of the photoacoustic image generation apparatus 10, and comprises a trigger control circuit (not shown) in the present embodiment. The trigger control circuit transmits a light emission trigger signal to the laser unit 13, for example, at the start of the photoacoustic image generation apparatus 10. Then, in the laser unit 13, a flash lamp is lit to start the excitation of the laser rod. Then, the excitation state of the laser rod is maintained, so that the laser unit 13 can output pulsed laser light.

Then, at the time of generating a photoacoustic image, the control unit 31 transmits a Qsw trigger signal to the laser unit 13 from the trigger control circuit. That is, the control unit 31 controls the output timing of the pulsed laser light from the laser unit 13 using the Qsw trigger signal. In the present embodiment, the control unit 31 transmits a sampling trigger signal to the AD converter 22 simultaneously with the transmission of the Qsw trigger signal. The sampling trigger signal is a signal of the start timing of the sampling of the photoacoustic wave signal in the AD converter 22. Thus, it is possible to sample the photoacoustic wave signal in synchronization with the output of laser light by using the sampling trigger signal.

At the time of generating an ultrasound image, the control unit 31 transmits an ultrasound wave transmission trigger signal for instructing the transmission control circuit 30 to transmit ultrasound waves. In a case where the trigger signal is received, the transmission control circuit 30 causes the ultrasound probe 11 to transmit ultrasound waves. After the transmission of ultrasound waves, the ultrasound probe 11 detects reflected ultrasound waves from the subject M and outputs a reflected wave signal.

The reflected wave signal output from the ultrasound probe 11 is input to the AD converter 22 through the reception circuit 21. The control unit 31 transmits a sampling trigger signal to the AD converter 22 according to the timing of ultrasound wave transmission, thereby starting the sampling of the reflected wave signal.

Then, in the present embodiment, the control unit 31 controls each unit so that the photoacoustic image and the ultrasound image are acquired at the same timing. The same timing referred to herein does not mean completely the same timing but means that the photoacoustic image and the ultrasound image are sequentially acquired within a short time of a predetermined timing. That is, the photoacoustic image and the ultrasound image are sequentially acquired at the same frame rate.

For example, the display control unit 29 displays the photoacoustic image and the ultrasound image separately on the display unit 14, or displays a composite image of the photoacoustic image and the ultrasound image on the display unit 14. The display control unit 29 performs image combination by superimposing the photoacoustic image and the ultrasound image, for example.

The display control unit 29 of the present embodiment displays, on the display unit 14, a blood vessel regeneration index indicating the state of the blood vessel by the regeneration treatment described above. The blood vessel regeneration index is acquired by the photoacoustic image evaluation unit 28. The configuration of the photoacoustic image evaluation unit 28 and the blood vessel regeneration index will be described in detail later.

The image storage unit 26 temporarily stores the photoacoustic image generated by the photoacoustic image generation unit 24 and the ultrasound image generated by the ultrasound image generation unit 25, and may be, for example, a storage medium such as a semiconductor memory or a hard disk. After the photoacoustic image and the ultrasound image are temporarily stored in the image storage unit 26, the photoacoustic image and the ultrasound image are sequentially stored in the past image storage unit 27 as a past photoacoustic image and a past ultrasound image.

The past image storage unit 27 stores the photoacoustic image and the ultrasound image captured in the past, and may be, for example, a storage medium such as a large capacity semiconductor memory or a hard disk. The past image storage unit 27 stores identification information, by which the subject M can be identified, and the photoacoustic image and the ultrasound image so as to be associated with each other. The identification information may be information by which a patient can be identified, or may be information by which a patient and its imaging part can be identified. In the present embodiment, the past image storage unit 27 is provided in the ultrasound unit 12, but the place to store past photoacoustic images and past ultrasound images is not limited thereto. For example, past photoacoustic images and past ultrasound images may be stored in an external image storage server or the like provided separately from the photoacoustic image generation apparatus 10 of the present embodiment.

The photoacoustic image evaluation unit 28 acquires the above-described blood vessel regeneration index based on the difference between the blood vessel included in the current photoacoustic image (corresponding to a first photoacoustic image) and the blood vessel included in the past photoacoustic image (corresponding to a second photoacoustic image). The blood vessel regeneration index acquired by the photoacoustic image evaluation unit 28 is output to the display control unit 29, and is displayed on the display unit 14 by the display control unit 29 as described above.

FIG. 3 is a diagram showing the internal configuration of the photoacoustic image evaluation unit 28. As shown in FIG. 3, the photoacoustic image evaluation unit 28 comprises a photoacoustic image acquisition unit 32, an image selection unit 33, a registration processing unit 34, a blood vessel region extraction unit 35, and a blood vessel regeneration index acquisition unit 36. These sections function by the control unit 31 that executes a photoacoustic image evaluation program installed on the memory as described above.

The photoacoustic image acquisition unit 32 reads and acquires the current photoacoustic image temporarily stored in the image storage unit 26, and reads and acquires the past photoacoustic image stored in the past image storage unit 27. Specifically, the photoacoustic image acquisition unit 32 acquires the current photoacoustic image from the image storage unit 26, and acquires the identification information of the subject M that is an imaging target of the current photoacoustic image. The identification information of the subject M is set and input by the user using the input unit 15, for example. Then, based on the acquired identification information, the photoacoustic image acquisition unit 32 reads and acquires the photoacoustic image and the ultrasound image obtained by imaging the same part of the same patient from the past image storage unit 27. In addition, the photoacoustic image acquisition unit 32 may acquire the past photoacoustic image and the past ultrasound image from an image storage server or the like provided outside as described above instead of from the past image storage unit 27.

In the present embodiment, as described above, the current photoacoustic image is stored in the image storage unit 26. In this case, not only one photoacoustic image but also a group of a series of consecutively captured photoacoustic images is stored. Then, the group of a series of photoacoustic images is also stored in the past image storage unit 27. It is desirable that the group of photoacoustic images is photoacoustic images of, for example, 50 frames or more and 100 frames or less. The group of a series of photoacoustic images is a group of photoacoustic images that can be subjected to registration processing to be described later. Hereinafter, the group of current photoacoustic images is referred to as a group of first photoacoustic image candidates, and the group of past photoacoustic images is referred to as a group of second photoacoustic image candidates. Also for the ultrasound image, a series of ultrasound images consecutively captured corresponding to the photoacoustic image are stored.

Then, the photoacoustic image acquisition unit 32 reads and acquires a group of first photoacoustic image candidates from the image storage unit 26, outputs the group of first photoacoustic image candidates to the image selection unit 33, reads and acquires a group of second photoacoustic image candidates from the past image storage unit 27, and outputs the group of second photoacoustic image candidates to the image selection unit 33.

The image selection unit 33 selects one first photoacoustic image, which is subjected to registration processing to be described later, from the input group of first photoacoustic image candidates, and selects one second photoacoustic image subjected to the registration processing from the input group of second photoacoustic image candidates. That is, the image selection unit 33 determines a combination of the first photoacoustic image and the second photoacoustic image, for which registration processing can be more easily performed, from the group of first photoacoustic image candidates and the group of second photoacoustic image candidates.

Figure 4:
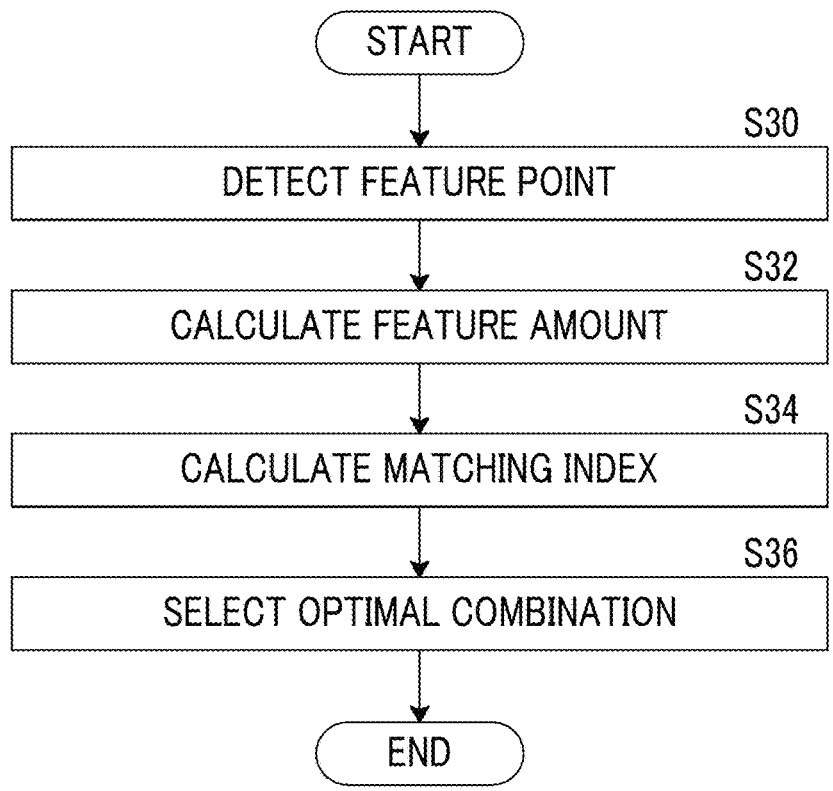
FIG. 4 is a flowchart illustrating an example of matching processing in an image selection unit.

Specifically, in a case where there are M first photoacoustic image candidates and N second photoacoustic image candidates, the image selection unit 33 performs matching processing M×N times. That is, the matching processing is performed for all combinations of the first photoacoustic image candidates and the second photoacoustic image candidates. FIG. 4 is a flowchart illustrating an example of the matching processing. As the matching processing, it is desirable to perform robust feature-based matching for image deformation. In the feature-based matching, as shown in FIG. 4, feature points such as edges or corners are first detected from images (S30). Then, feature amounts (local descriptors) are calculated from local regions around the feature points (S32). Then, matching between the first photoacoustic image and the second photoacoustic image is performed based on the distance of the feature amount, and a matching index indicating the degree of matching is calculated for all combinations (S34). Then, the image selection unit 33 selects a combination of the first photoacoustic image and the second photoacoustic image having the highest matching index as an optimal combination (S36).

For extraction of feature points, it is possible to use methods, such as Harris point, difference of Gaussian (DoG) region, Harris-Affine region, and maximally stable extremal regions (MSER). As the feature amount, it is possible to use scale invariant feature transform (SIFT), gradient location-orientation histogram (GLOH), and the like.

In the present embodiment, as described above, matching processing is performed for all combinations of the first photoacoustic image candidates and the second photoacoustic image candidates. However, the present invention is not limited thereto. The user may select one second photoacoustic image, among N second photoacoustic image candidates, for the past second photoacoustic image, and matching between the selected second photoacoustic image and M first photoacoustic image candidates may be performed. In this manner, it is possible to shorten the time of matching processing. Conversely, the user may select one first photoacoustic image, among M first photoacoustic image candidates, for the current first photoacoustic image, and matching between the selected first photoacoustic image and N second photoacoustic image candidates may be performed.

For the user's selection of the first photoacoustic image or the second photoacoustic image, for example, the display control unit 29 may display M first photoacoustic image candidates or N second photoacoustic image candidates on the display unit 14 so that the user selects one first photoacoustic image or one second photoacoustic image among the displayed first photoacoustic image candidates or second photoacoustic image candidates using the input unit 15.

In the present embodiment, as described above, the combination of the first photoacoustic image and the second photoacoustic image having the highest matching index is selected as an optimal combination. However, the present invention is not limited thereto. A preset number of combinations may be selected in order from the combination having the highest matching index, and the display control unit 29 may display the plurality of combinations on the display unit 14. Then, the user may select one combination among the plurality of combinations using the input unit 15.

In a case where the highest matching index is equal to or less than a threshold value set in advance, a message or the like may be displayed on the display unit 14 in order to prompt the user to capture the group of first photoacoustic image candidates again.

Figure 5:
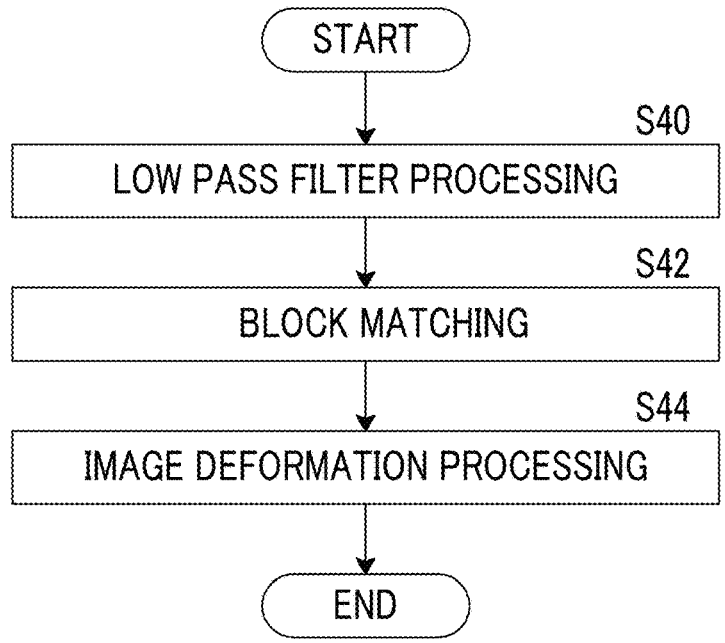
FIG. 5 is a flowchart illustrating an example of registration processing in a registration processing unit.

The registration processing unit 34 performs registration processing between the first photoacoustic image and the second photoacoustic image selected by the image selection unit 33. FIG. 5 is a flowchart illustrating an example of the registration processing in the registration processing unit 34 of the present embodiment. In the present embodiment, in order to perform registration with high accuracy, registration processing between relatively thick blood vessels, among blood vessels included in the first photoacoustic image and the second photoacoustic image, is performed. Specifically, image components of blood vessels having thicknesses of 300 μm or more are extracted by performing low pass filter processing on the first photoacoustic image and the second photoacoustic image (S40). The cutoff frequency of the low pass filter is set so as to extract image components of blood vessels having thicknesses of 300 μm or more.

Then, blocking matching is performed between the first photoacoustic image and the second photoacoustic image after the low pass filter processing to estimate a movement vector (S42). Then, image deformation processing is performed based on the movement vector (S44). In the image deformation processing, the current first photoacoustic image may be deformed with the past second photoacoustic image as a reference, or the past second photoacoustic image may be deformed with the current first photoacoustic image as a reference. As the registration processing, other known methods can be used without being limited to the blocking matching described above.

In the present embodiment, registration processing between thick blood vessels is performed for all of the first photoacoustic images and the second photoacoustic images. However, the present invention is not limited thereto. Some reference regions may be set in the first photoacoustic images and the second photoacoustic images, and registration processing may be performed so that the accuracy of registration between the reference regions is improved. Some reference regions are set in such a manner that the display control unit 29 displays a first photoacoustic image and a second photoacoustic image on the display unit 14 and the user designates some regions in the first photoacoustic image and the second photoacoustic image using the input unit 15, for example.

As the reference region, for example, a region including blood vessels having thicknesses of 300 μm or more as described above may be designated with a region, in which it is estimated that blood vessels are regenerated by regeneration treatment, as the center.

Examples of the movement vector estimation method described above include a method of evaluating similarity, such as a normalized correlation function, for each block, a method of extracting key points (for example, specific patterns such as corners) from the entire image and estimating the movement vector based on the key points, and the like. However, other known methods may be used without being limited to these methods.

Then, the blood vessel region extraction unit 35 extracts a blood vessel region from each of the first photoacoustic image and the second photoacoustic image subjected to registration processing by the registration processing unit 34. In this specification, a blood vessel region extracted from the first photoacoustic image is referred to as a first blood vessel region, and a blood vessel region extracted from the second photoacoustic image is referred to as a second blood vessel region.

As blood vessel region extraction processing, first, emphasis processing on a line structure is performed using a Hessian filter. Specifically, a Hessian operator is applied to local regions of the first photoacoustic image and the second photoacoustic image to acquire a Hessian matrix configured to include second-order differential components of the local region, and then eigenvalues are calculated by matrix diagonalization. In a case where the image is a two-dimensional image, two eigenvalues $\lambda 1$ and $\lambda 2$ are calculated. In a case where the image is a three-dimensional image, three eigenvalues $\lambda 1$ to $\lambda 3$ are calculated. Then, a line structure or a mass structure included in the local region can be extracted by using a discriminant expressing the relationship between the magnitudes of the calculated eigenvalues. Specifically, for example, the local region is a line structure in the case of $\lambda 1 \gg 0$ and $\lambda 2 \cong 0$, and the local region is a mass structure in the case of $\lambda 1 \gg 0$ and $\lambda 2 \gg 0$.

Then, by performing binarization processing for threshold value determination after performing the line structure emphasis processing using a Hessian filter on the first photoacoustic image and the second photoacoustic image, it is possible to extract a blood vessel region.

In addition to the emphasis processing using the Hessian filter described above, in a case where the first photoacoustic image and the second photoacoustic image are two-dimensional images, emphasis processing using a Gabor filter may be adopted. The Gabor filter performs maximum output in a case where the thicknesses of the filter shape and the line structure are the same. Filter characteristics are determined from the resolution [pixel/μm] of the first photoacoustic image and the second photoacoustic image and the diameter [μm] of a blood vessel to be extracted. Then, by performing binarization processing for threshold value determination after performing emphasis processing on the first photoacoustic image and the second photoacoustic image using the Hessian filter, it is possible to extract a blood vessel region having a desired diameter. The emphasis processing using the Gabor filter is performed while changing the angle θ of the line structure. However, in a case where the direction in which the blood vessel extends is known in advance, the change range of the angle θ may be limited. The change range of the angle θ may be set and input by the user using the input unit 15.

In addition, it is desirable that a blood vessel to be extracted by blood vessel region extracting processing is 30 μm or more and 300 μm or less. Therefore, for example, the diameters of a plurality of blood vessels may be set, the above-described blood vessel extraction processing may be performed for each diameter, and blood vessels of respective diameters may be integrated to acquire one first blood vessel region and one second blood vessel region.

Specifically, for example, in the case of performing emphasis processing using the Hessian filter described above, by adjusting σ of the Gaussian filter of the Hessian operator represented by the differential filter×Gaussian filter according to the desired blood vessel diameter, it is possible to specifically extract a signal corresponding to the blood vessel having the desired diameter. In the case of extracting blood vessels having diameters of 30 μm or more and 300 μm or less as described above, a plurality of σ corresponding to blood vessel diameters, such as σ1=30 μm to 100 μm, σ2=100 μm to 200 μm, and σ3=200 μm to 300 μm, may be set, and the blood vessel extraction processing may be performed multiple times. Alternatively, σ may be fixed and multiple resolutions of the first photoacoustic image and the second photoacoustic image may be set to perform processing equivalent to changing σ.

In the case of performing emphasis processing using the Gabor filter described above, filter characteristics corresponding to the diameters of a plurality of blood vessels may be set.

In the above description, the line structure is extracted as a blood vessel region. However, in a case where the azimuth direction of the ultrasound probe 11 (arrangement direction of the ultrasound transducers 20a) and the direction in which the blood vessel extends are not parallel but, for example, perpendicular to each other, the blood vessel region appears not as a line structure but as a dot-like mass structure in the first photoacoustic image and the second photoacoustic image. Therefore, such a dot-like mass structure may also be extracted as a blood vessel region.

For example, a dot-like mass structure may be extracted by emphasis processing using the Hessian filter described above. The present invention is not limited thereto. In a case where the brightness of the blood vessel region and the shape of the mass structure are uniform to some extent, a dot-like mass structure may be extracted using template matching. In a case where there are some variations in the brightness of the blood vessel region and the shape of the mass structure, a discriminator may be generated by learning a feature vector using machine learning, such as Adaboost, using a feature amount abstracting the brightness or the shape, and a dot-like mass structure may be extracted using the discriminator. Alternatively, after binarizing the first photoacoustic image and the second photoacoustic image, a dot-like mass structure may be extracted using a morphology filter.

Then, the blood vessel regeneration index acquisition unit 36 acquires a blood vessel regeneration index based on the difference between the first blood vessel region and the second blood vessel region extracted by the blood vessel region extraction unit 35. As described above, the blood vessel regeneration index indicates the state of the blood vessel by regeneration treatment.

As a specific example of the blood vessel regeneration index, for example, there is a degree of increase of a blood vessel. The degree of increase (%) of a blood vessel can be calculated, for example, by dividing the number of pixels included in the first blood vessel region by the number of pixels included in the second blood vessel region and multiplying the result of the division by 100. Alternatively, the degree of increase (%) of a blood vessel may be calculated by dividing the area of the first blood vessel region by the area of the second blood vessel region and multiplying the result of the division by 100. The blood vessel regeneration index is not limited to the degree of increase described above. For example, by calculating the length of the first blood vessel region and the length of the second blood vessel region and subtracting the length of the second blood vessel region from the length of the first blood vessel region, the length of the blood vessel increased by the regeneration treatment may be calculated as the blood vessel regeneration index. Alternatively, by subtracting the area of the second blood vessel region from the area of the first blood vessel region, the area of the blood vessel increased by the regeneration treatment may be calculated as the blood vessel regeneration index.

Figure 6:
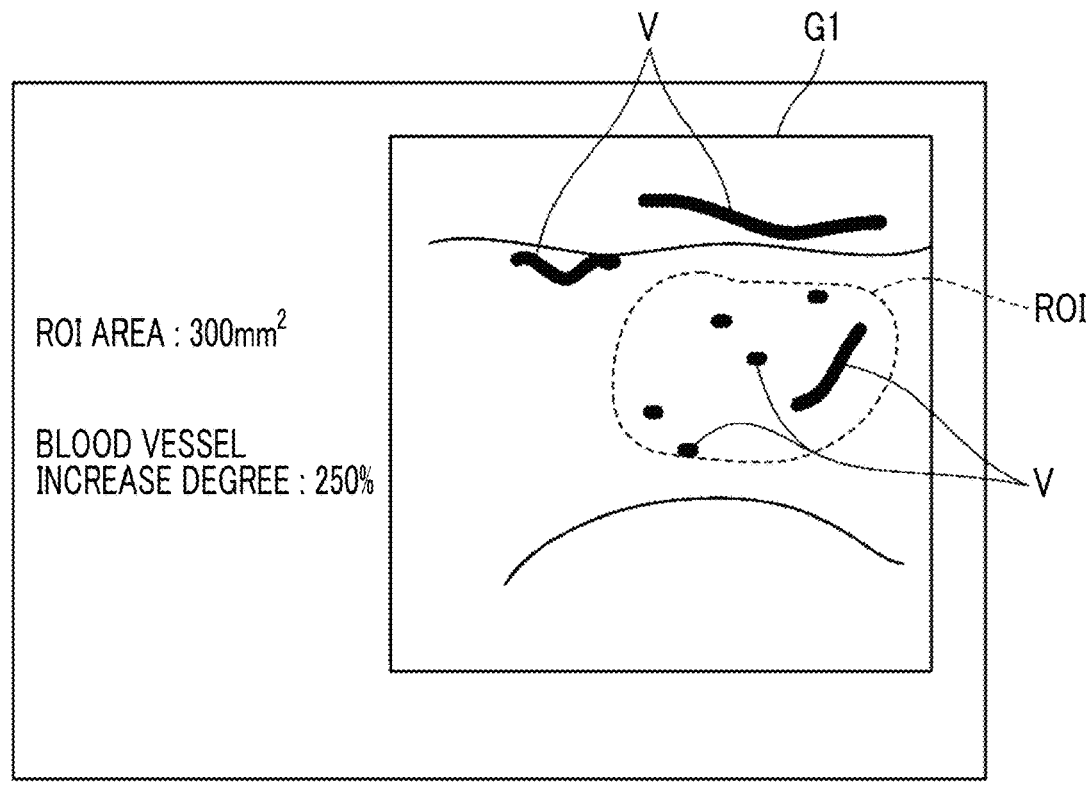
FIG. 6 is a diagram showing a display example of a blood vessel regeneration index.

Then, the blood vessel regeneration index acquired by the blood vessel regeneration index acquisition unit 36 is output to the display control unit 29, and the display control unit 29 displays the blood vessel regeneration index on the display unit 14. FIG. 6 is a diagram showing an example in which the degree of increase of a blood vessel is displayed as a blood vessel regeneration index. FIG. 6 shows an example in which a composite image G1 of a first photoacoustic image (current photoacoustic image) and an ultrasound image captured at the same timing as the first photoacoustic image, the range of a region of interest (ROI) in the composite image G1, the area of the ROI, and the degree of increase of the blood vessel in the ROI are displayed. "V" shown in FIG. 6 is the first blood vessel region in the first photoacoustic image.

The ROI may be set and input by the user using the input unit 15, for example. Alternatively, a reference region designated at the time of the above-described registration processing may be set as the ROI.

Figure 7:
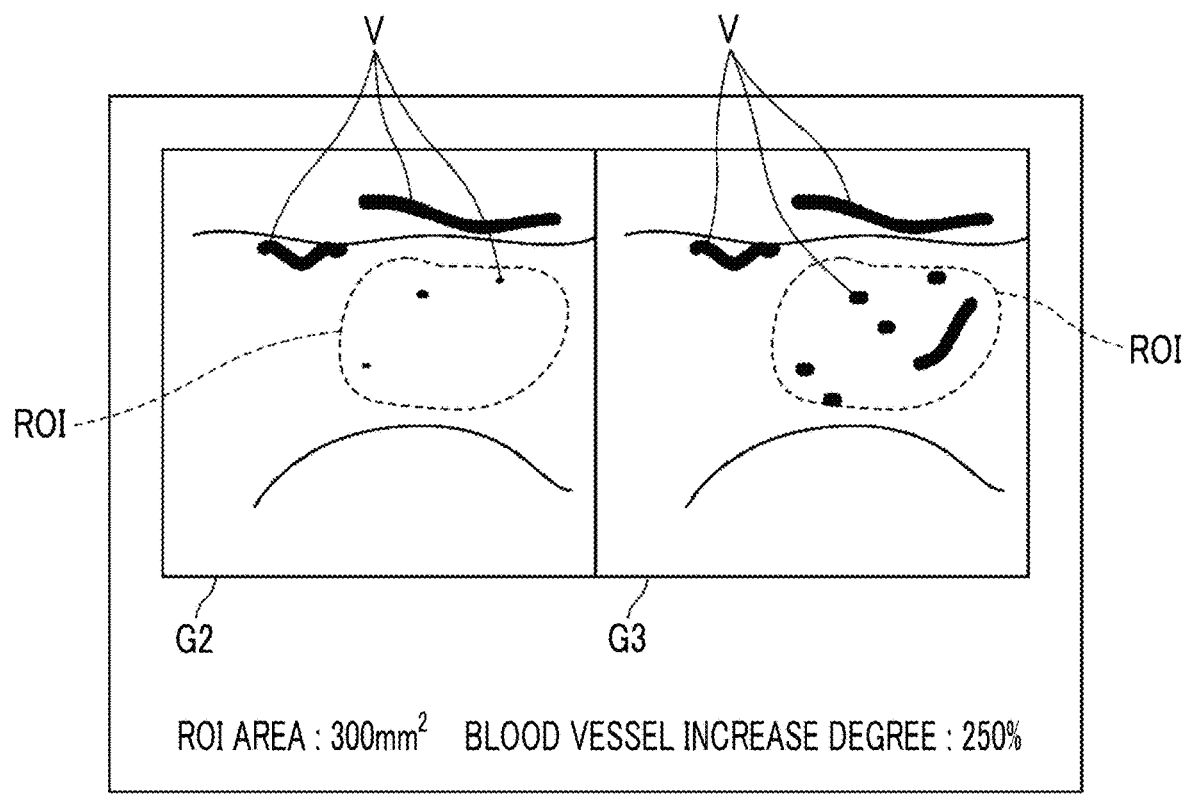
FIG. 7 is a diagram showing other display examples of the blood vessel regeneration index.

In FIG. 6, the composite image G1 of the first photoacoustic image (current photoacoustic image) and the ultrasound image captured at the same timing as the first photoacoustic image is displayed. However, the present invention is not limited thereto. As shown in FIG. 7, a composite image G2 of a second photoacoustic image (past photoacoustic image) and an ultrasound image captured at the same timing as the second photoacoustic image and a composite image G3 of a first photoacoustic image (current photoacoustic image) and an ultrasound image captured at the same timing as the first photoacoustic image may be displayed side by side.

Figure 8:
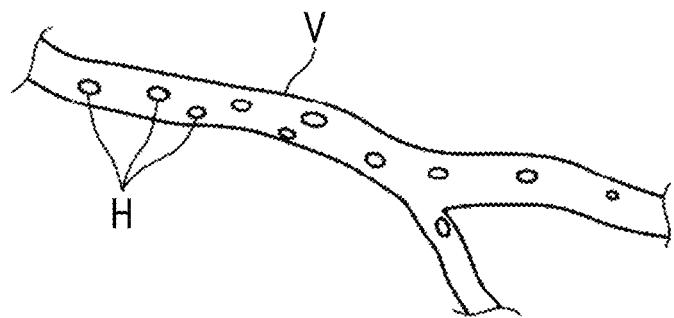
FIG. 8 is a diagram showing an example of a first blood vessel pattern extending continuously over a preset length or more.
Figure 9:
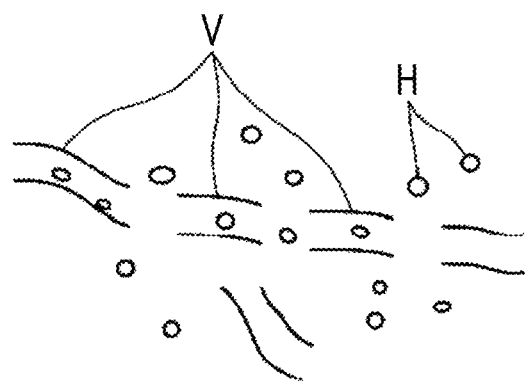
FIG. 9 is a diagram showing an example of a second blood vessel pattern in which a plurality of partial blood vessel regions having a preset length or less are intermittently distributed.

As a pattern of the shape of a blood vessel region V regenerated by regeneration treatment, a first blood vessel pattern, which extends continuously over a preset length or more as shown in FIG. 8, and a second blood vessel pattern, in which a plurality of partial blood vessel regions having the preset length or less are intermittently distributed as shown in FIG. 9, can be considered. Therefore, for example, it may be determined whether a region excluding the second blood vessel region from the first blood vessel region, that is, the pattern of the shape of the blood vessel region regenerated by the regeneration treatment, is a first blood vessel pattern or a second blood vessel pattern, and the determination result may be displayed on the display unit 14 as a blood vessel regeneration index. As a method of distinguishing between the first blood vessel pattern and the second blood vessel pattern, for example, not only the region excluding the second blood vessel region from the first blood vessel region but also a region of hemoglobin H is extracted, and a group of pixels belonging to these regions is specified as a regenerated blood vessel region. In the case of the second blood vessel pattern shown in FIG. 9, it is estimated that hemoglobin oozes out to the surrounding tissue since a partial blood vessel region is intermittently regenerated. That is, in the case of the second blood vessel pattern shown in FIG. 9, the regenerated blood vessel region is a region that does not extend linearly but spreads in a two-dimensional manner. Therefore, the degree of extension of the regenerated blood vessel region may be calculated, and the first blood vessel pattern and the second blood vessel pattern may be distinguished based on the degree of extension. For the degree of extension, for example, a long axis and a short axis may be calculated from the center-of-gravity secondary moment of the regenerated blood vessel region, and the ratio of the long axis to the short axis may be calculated as the degree of extension. In a case where the degree of extension is equal to or greater than a preset threshold value, determination as a first blood vessel pattern may be made. In a case where the degree of extension is less than the threshold value, determination as a second blood vessel pattern may be made. Alternatively, the first blood vessel pattern and the second blood vessel pattern may be distinguished based on the total number of pixels of the region excluding the second blood vessel region from the first blood vessel region. Specifically, in a case where the total number of pixels is equal to or greater than a preset threshold value, determination as a first blood vessel pattern may be made. In a case where the total number of pixels is less than the threshold value, determination as a second blood vessel pattern may be made.

In addition, it may be determined whether the blood vessel region regenerated by the regeneration treatment is a first blood vessel pattern or a second blood vessel pattern, and the proportion of each of the first blood vessel pattern and the second blood vessel pattern included in the first photoacoustic image (current photoacoustic image) may be calculated, and a blood vessel pattern having a larger proportion may be determined as a blood vessel pattern as the entire first photoacoustic image.

Figure 10:
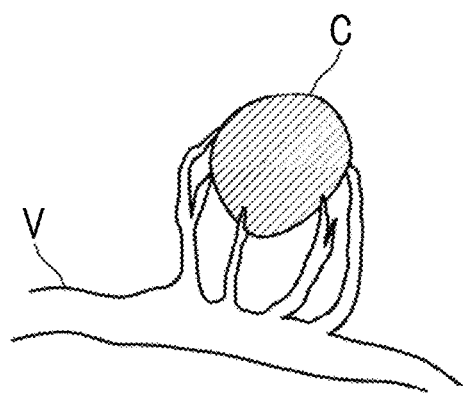
FIG. 10 is a diagram showing an example of a blood vessel pattern of cancer tissue.

It may be determined whether the blood vessel regenerated by the regeneration treatment is a normal regenerated blood vessel or a blood vessel of cancer tissue, and the determination result may be acquired as a blood vessel regeneration index. As a method of determining whether the blood vessel regenerated by the regeneration treatment is a normal regenerated blood vessel or a regenerated blood vessel of cancer tissue, for example, the determination may be made based on the pattern of the shape of the blood vessel region regenerated by the regeneration treatment. Specifically, in the case of a normal regenerated blood vessel, as shown in FIG. 8, a shape pattern extending linearly to some extent is obtained. However, in the case of a regenerated blood vessel of cancer tissue, as shown in FIG. 10, the blood vessel region V is a pattern having such a shape as to surround cancer tissue C. Therefore, a difference in the pattern of the shape of the blood vessel region V may be determined. Alternatively, the amount of deviation from the pattern of the shape of the normal regenerated blood vessel shown in FIG. 8 may be calculated, and whether the blood vessel regenerated by the regeneration treatment is a normal regenerated blood vessel or a regenerated blood vessel of cancer tissue may be determined based on the amount of deviation.

In addition, the risk of a disease of a current subject (patient) may be acquired based on the increase amount of the blood vessel regenerated by regeneration treatment, and the risk of the disease may be displayed as the blood vessel regeneration index. As the risk of the disease, for example, there is a risk of cutting hands or legs due to diabetes. As a method of acquiring the risk of the disease, for example, as shown in FIG. 11, a table in which the increase amount (%) of the blood vessel regenerated by the regeneration treatment is associated with the risk of the disease may be set in advance. In the case of a table shown in FIG. 11, it means that the greater the numerical value of the risk, the higher the risk of cutting.

Returning to FIG. 1, the display unit 14 comprises a display device such as a liquid crystal display, for example. The input unit 15 comprises an input device, such as a keyboard and a mouse. By using a touch panel, the display unit 14 and the input unit 15 may be used in common.

Figure 12:
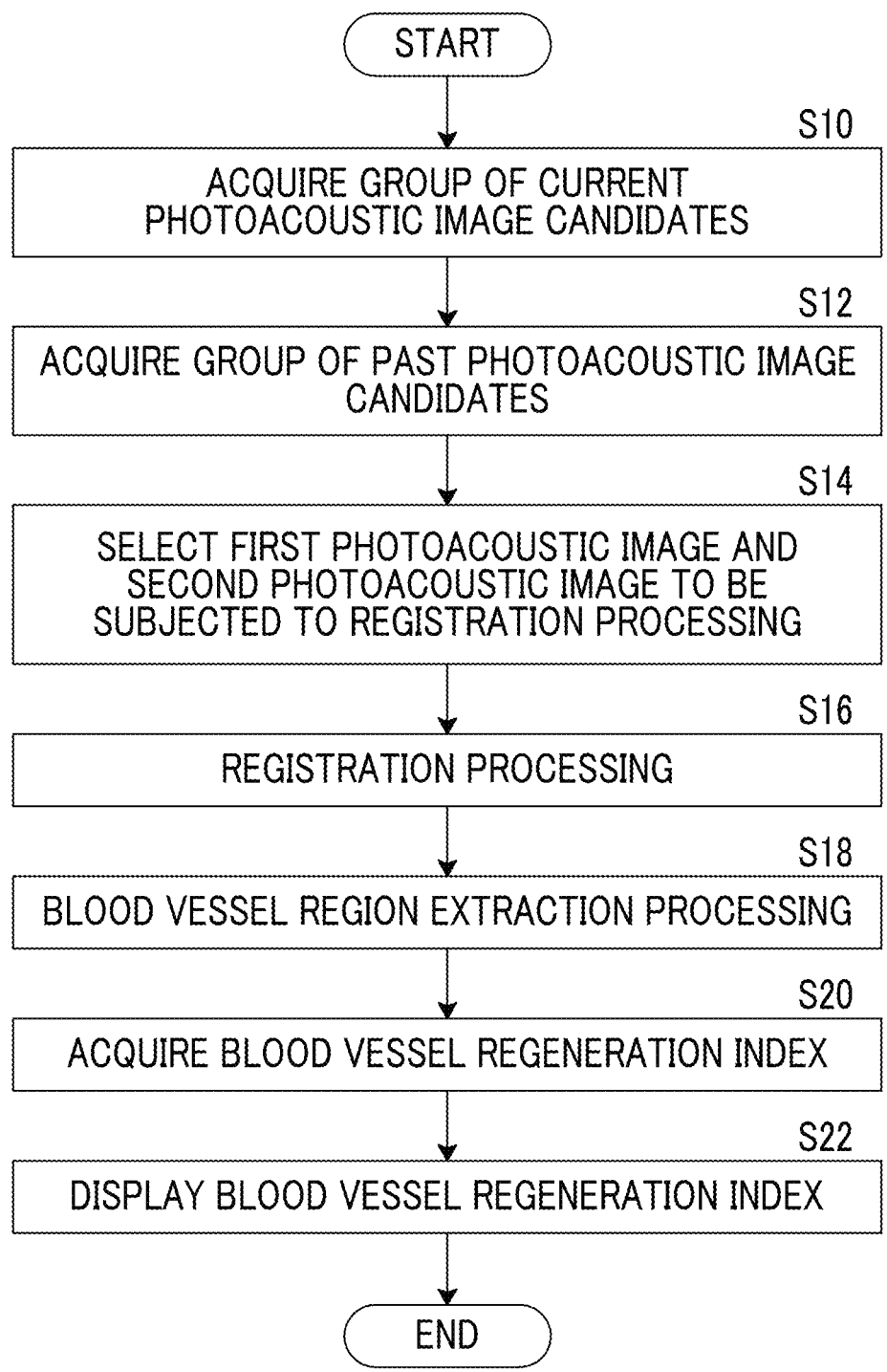
FIG. 12 is a flowchart illustrating the operation of the photoacoustic image generation apparatus using an embodiment of the photoacoustic image evaluation apparatus of the present invention.

Next, the operation of the photoacoustic image generation apparatus 10 of the present embodiment will be described with reference to the flowchart shown in FIG. 12. In addition, since the photoacoustic image generation apparatus 10 of the present embodiment is characterized by the photoacoustic image evaluation unit 28, the operation of the photoacoustic image evaluation unit 28 will mainly be described.

First, the photoacoustic image acquisition unit 32 reads and acquires a group of first photoacoustic image candidates from the image storage unit 26 (S10).

Then, the photoacoustic image acquisition unit 32 reads and acquires a group of second photoacoustic image candidates from the past image storage unit 27 (S12).

Then, the group of first photoacoustic image candidates and the group of second photoacoustic image candidates acquired by the photoacoustic image acquisition unit 32 are output to the image selection unit 33, and the image selection unit 33 selects one first photoacoustic image to be subjected to registration processing from the group of first photoacoustic image candidates and selects one second photoacoustic image to be subjected to registration processing from the group of second photoacoustic image candidates (S14).

The first photoacoustic image and the second photoacoustic image selected by the image selection unit 33 are output to the registration processing unit 34, and registration processing is performed on the first photoacoustic image and the second photoacoustic image by the registration processing unit 34 (S16).

Then, the first photoacoustic image and the second photoacoustic image after the registration processing are output to the blood vessel region extraction unit 35, and the blood vessel region extraction unit 35 extracts a first blood vessel region from the first photoacoustic image and extracts a second blood vessel region from the second photoacoustic image (S18).

Then, information of the photoacoustic images of the first blood vessel region and the second blood vessel region is output to the blood vessel regeneration index acquisition unit 36, and the blood vessel regeneration index acquisition unit 36 acquires the above-described blood vessel regeneration index based on the information of the photoacoustic images of the first blood vessel region and the second blood vessel region (S20).

The blood vessel regeneration index acquired by the blood vessel regeneration index acquisition unit 36 is output to the display control unit 29, and the display control unit 29 displays the input blood vessel regeneration index on the display unit 14 (S22).

According to the photoacoustic image generation apparatus 10 of the embodiment described above, a first photoacoustic image generated at a first point in time and a second photoacoustic image generated at a second point in time before the first point in time are acquired, a blood vessel regeneration index indicating the state of a blood vessel by regeneration treatment is acquired based on the difference between a blood vessel included in the first photoacoustic image and a blood vessel included in the second photoacoustic image, and the blood vessel regeneration index is displayed on the display unit 14. Therefore, it is possible to easily and highly accurately check the effect of blood vessel regeneration treatment.

In the above description, the first blood vessel region and the second blood vessel region are respectively extracted from the first photoacoustic image and the second photoacoustic image after the registration processing. However, the procedure of the processing is not limited thereto. For example, registration processing between the first photoacoustic image and the second photoacoustic image and blood vessel extraction processing of the first blood vessel region and the second blood vessel region may be performed in parallel. Specifically, information of a movement vector may be acquired by registration processing between the first photoacoustic image and the second photoacoustic image, and in parallel with this, blood vessel extraction processing of the first blood vessel region and the second blood vessel region may be performed. Using the information of the movement vector described above, image deformation processing of the first blood vessel region and the second blood vessel region may be performed.

Figure 13:
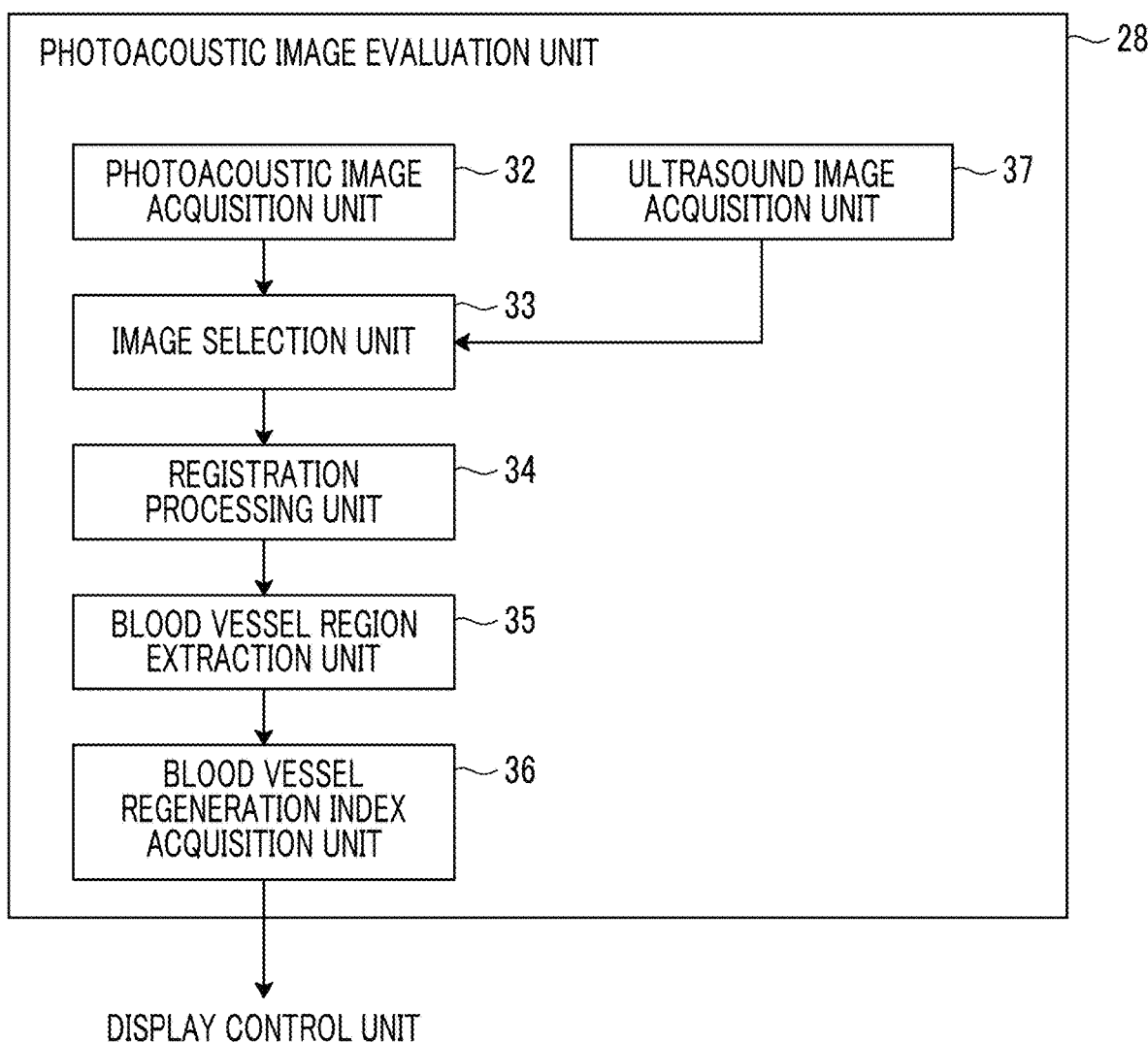
FIG. 13 is a block diagram showing another embodiment of the photoacoustic image evaluation unit.

In the embodiment described above, the movement vector may be estimated from the first photoacoustic image and the second photoacoustic image to perform the registration processing. However, the present invention is not limited thereto. A movement vector may be estimated using the ultrasound image generated by the ultrasound image generation unit 25 and registration processing between the first photoacoustic image and the second photoacoustic image may be performed using the movement vector. FIG. 13 is a diagram showing a specific configuration for performing registration processing between a first photoacoustic image and a second photoacoustic image using an ultrasound image.

An ultrasound image acquisition unit 37 acquires a group of current ultrasound images stored in the image storage unit 26, and acquires a group of past ultrasound images stored in the past image storage unit 27. The group of current ultrasound images (hereinafter, referred to as a group of first ultrasound image candidates) is detected at the same scan as the group of first photoacoustic image candidates described above, and the group of past ultrasound images (hereinafter, referred to as a group of second ultrasound image candidates) is detected at the same scan as the group of second photoacoustic image candidates described above.

Then, the group of first ultrasound image candidates and the group of second ultrasound image candidates are output to the image selection unit 33. By performing the same matching processing as in the embodiment described above on the group of first ultrasound image candidates and the group of second ultrasound image candidates, the image selection unit 33 selects a first ultrasound image to be subjected to registration processing from the group of first ultrasound image candidates and selects a second ultrasound image to be subjected to registration processing from the group of second ultrasound image candidates, and outputs the first ultrasound image and the second ultrasound image to the registration processing unit 34. In addition, the image selection unit 33 selects a first photoacoustic image detected at the same timing as the first ultrasound image and a second photoacoustic image detected at the same timing as the second ultrasound image, and outputs the first photoacoustic image and the second photoacoustic image to the registration processing unit 34.

Then, the registration processing unit 34 performs registration processing between the first ultrasound image and the second ultrasound image to acquire information of the movement vector, and performs registration processing between the first photoacoustic image and the second photoacoustic image using the information of the movement vector.

The ultrasound image includes structures such as bones and organs that are difficult to appear in the photoacoustic image. Therefore, by performing registration processing using structures such as bones with less deformation and organs with small amounts of movement, it is possible to perform more accurate registration.

In the embodiment described above, a group of a series of consecutively generated photoacoustic image candidates is acquired and stored in the past image storage unit 27. In this case, information of the position and posture of the ultrasound probe 11 with respect to the subject M may also be acquired and stored in association with the group of photoacoustic image candidates. Then, at the time of acquiring a group of current first photoacoustic image candidates, information of the position and posture of the ultrasound probe 11 stored in association with the past second photoacoustic image candidates is acquired. Then, information of the position and posture of the ultrasound probe 11 capable of imaging a range equivalent to the imaging range specified by these pieces of information or a wider range may be displayed on the display unit 14 or the like in order to notify the user of the information. The information of the position and posture of the ultrasound probe 11 may be acquired by providing an acceleration sensor, a magnetic sensor, or the like in the ultrasound probe 11.

After a group of a series of photoacoustic image candidates is temporarily stored in the past image storage unit 27, unnecessary photoacoustic image candidates may be deleted.

Specifically, the image selection unit 33 may select a photoacoustic image candidate whose signal strength is equal to or less than a preset threshold value from the group of a series of photoacoustic image candidates and delete the selected photoacoustic image candidate from the past image storage unit 27. In addition, a blur detection unit (not shown) that detects blur of each photoacoustic image candidate may be provided, and the image selection unit 33 may select a photoacoustic image candidate whose blur amount is equal to or greater than a preset threshold value and delete the selected photoacoustic image candidate from the past image storage unit 27. Alternatively, the image selection unit 33 may perform matching processing between photoacoustic image candidates included in the group of a series of photoacoustic image candidates stored in the past image storage unit 27, and any one of the photoacoustic image candidates may be deleted from the past image storage unit 27 for a combination of photoacoustic image candidates for which a matching index is higher than a preset threshold value.

By selectively deleting some photoacoustic image candidates and storing the remaining photoacoustic image candidates in the past image storage unit 27 as described above, it is possible to reduce the storage capacity of the past image storage unit 27, and it is possible to shorten the time required for matching processing between the first photoacoustic image candidate and the second photoacoustic image candidate in the image selection unit 33.

The image selection unit 33 may acquire a group of ultrasound images acquired at the same scan as the group of second photoacoustic image candidates, specify an ultrasound image including, for example, a characteristic pattern, such as a bone or an organ, from the group of ultrasound images, select only the second photoacoustic image candidate acquired at the same timing as the specified ultrasound image, and store the selected second photoacoustic image candidate in the past image storage unit 27.

At the time of capturing the current first photoacoustic image, the second photoacoustic image candidate selectively stored in the past image storage unit 27 as described above may be displayed on the display unit 14 to prompt the user to image the same part or the same cross section.

After the first photoacoustic image and the second photoacoustic image are once selected by the image selection unit 33, that is, at the time of capturing a photoacoustic image third and subsequent times, the selected first photoacoustic image and second photoacoustic image may be displayed on the display unit 14 in order to prompt the user to image the same part or the same cross section.

In the case of selecting a second photoacoustic image to be subjected to registration processing from the group of second photoacoustic image candidates, the image selection unit 33 may select a second photoacoustic image with which more accurate registration processing is possible. For example, a second photoacoustic image candidate with a clear traveling of a blood vessel may be selected as the second photoacoustic image to be subjected to the registration processing. In this case, for example, the sharpness of each photoacoustic image candidate included in the group of second photoacoustic image candidates may be acquired, and a photoacoustic image candidate having the highest sharpness may be selected as the second photoacoustic image to be subjected to the registration processing. In addition, only the second photoacoustic image candidate whose sharpness is equal to or greater than a preset threshold value may be stored in the past image storage unit 27.

In the case of selecting a second photoacoustic image to be subjected to registration processing from the group of second photoacoustic image candidates, the image selection unit 33 may select a second photoacoustic image candidate, which includes an image of an insert that is inserted into the subject M at the time of performing regeneration treatment, as the second photoacoustic image to be subjected to the registration processing. Examples of the insert described above include a needle, such as a syringe needle used to inject bone marrow cells into the subject M at the time of performing blood vessel regeneration treatment, and other catheters.

In the case of acquiring the blood vessel regeneration index in the ROI as in the embodiment described above, the ROI may be set based on the position of the image of the needle included in the second photoacoustic image described above. Specifically, the ROI may be set at a position spaced apart from the distal end of the needle by a distance set in advance.

In the embodiment described above, the blood vessel regeneration index may be acquired in time series, and the numerical values may be displayed on the display unit 14 at the same time or the numerical values may be displayed in the form of a graph on the display unit 14.

In the embodiment described above, the first photoacoustic image and the second photoacoustic image acquired by the photoacoustic image acquisition unit 32 may be two-dimensional images or may be three-dimensional images.

While the present invention has been described based on the preferred embodiments thereof, the photoacoustic image evaluation apparatus and the photoacoustic image generation apparatus of the present invention are not limited only to the embodiments described above, and various modifications and changes from the configuration of the above-described embodiments are also included in the scope of the present invention.

EXPLANATION OF REFERENCES

10: photoacoustic image generation apparatus
11: ultrasound probe
11a: housing
12: ultrasound unit
13: laser unit
14: display unit
15: input unit
20: transducer array
20a: ultrasound transducer
21: reception circuit
22: AD converter
23: reception memory
24: photoacoustic image generation unit
25: ultrasound image generation unit
26: image storage unit
27: past image storage unit
28: photoacoustic image evaluation unit
29: display control unit
30: transmission control circuit
31: control unit
32: photoacoustic image acquisition unit
33: image selection unit
34: registration processing unit
35: blood vessel region extraction unit
36: blood vessel regeneration index acquisition unit
37: ultrasound image acquisition unit
40: cable
41: bundle fiber
41a: optical fiber
42 light emitting unit
C: cancer tissue
G: composite image
G1: composite image
G2: composite image
H: hemoglobin
L: measurement light
M: subject
U: photoacoustic wave
V: blood vessel region

What is claimed is:

1. A photoacoustic image evaluation apparatus comprising:
   a processor configured to:
   acquire a first photoacoustic image generated at a first point in time and a second photoacoustic image generated at a second point in time before the first point in time, the first and second photoacoustic images being photoacoustic images generated by detecting photoacoustic waves generated inside a subject, who has been subjected to blood vessel regeneration treatment, by emission of light into the subject;
acquire a blood vessel regeneration index, which indicates a state of a blood vessel by the regeneration treatment, based on a difference between a blood vessel included in the first photoacoustic image and a blood vessel included in the second photoacoustic image; and
display the blood vessel regeneration index on a display.

2. The photoacoustic image evaluation apparatus according to claim 1, wherein the processor is further configured to:
perform registration processing between the first photoacoustic image and the second photoacoustic image; and
extract a first blood vessel region included in the first photoacoustic image and a second blood vessel region included in the second photoacoustic image,
wherein the processor acquires the blood vessel regeneration index based on a difference between the first blood vessel region and the second blood vessel region registered by the registration processing.

3. The photoacoustic image evaluation apparatus according to claim 2,
wherein the processor acquires a group of a series of first photoacoustic image candidates consecutively generated at the first point in time, and
the processor is further configured to select the first photoacoustic image, which is to be subjected to the registration processing with the second photoacoustic image, from the group of first photoacoustic image candidates.

4. The photoacoustic image evaluation apparatus according to claim 2,
wherein the processor acquires a group of a series of second photoacoustic image candidates consecutively generated at the second point in time, and
the processor is further configured to select the second photoacoustic image, which is to be subjected to the registration processing with the first photoacoustic image, from the group of second photoacoustic image candidates.

5. The photoacoustic image evaluation apparatus according to claim 4,
wherein the processor selects the second photoacoustic image based on an image feature amount of the second photoacoustic image candidate.

6. The photoacoustic image evaluation apparatus according to claim 5,
wherein the processor selects the second photoacoustic image candidate, which includes an image of an insert that is inserted into the subject at the time of performing the regeneration treatment, as the second photoacoustic image.

7. The photoacoustic image evaluation apparatus according to claim 6, further comprising:
a past image storage that stores the second photoacoustic image,
wherein the past image storage stores only the second photoacoustic image selected from the group of second photoacoustic image candidates by the processor.

8. The photoacoustic image evaluation apparatus according to claim
wherein the processor acquires a group of a series of first photoacoustic image candidates consecutively generated at the first point in time and a group of a series of second photoacoustic image candidates consecutively generated at the second point in time, and the processor is further configured to select the first photoacoustic image, which is to be subjected to the registration processing with the second photoacoustic image, from the group of first photoacoustic image candidates and select the second photoacoustic image, which is to be subjected to the registration processing with the first photoacoustic image, from the group of second photoacoustic image candidates.

9. The photoacoustic image evaluation apparatus according to claim 2,
wherein the processor performs registration processing between the first photoacoustic image and the second photoa.coustic image based on some reference regions set in the first photoacoustic image and the second photoacoustic image.

10. The photoacoustic image evaluation apparatus according to claim 2, wherein the processor is further configured to:
acquire a first ultrasound image corresponding to the first photoacoustic image and a second ultrasound image corresponding to the second photoacoustic image, the first and second ultrasound images being ultrasound images generated by detecting reflected ultrasound waves that are reflected inside the subject by emission of ultrasound waves to the subject,
wherein the processor performs registration processing between the first photoacoustic image and the second photoacoustic image based on the first ultrasound image and the second ultrasound image.

11. The photoacoustic image evaluation apparatus according to claim 2,
wherein the processor performs the registration processing based on a blood vessel having a preset thickness or more.

12. The photoacoustic image evaluation apparatus according to claim 11,
wherein the processor performs low pass filter processing on the first photoacoustic image and the second photoacoustic image and performs the registration processing on the first photoacoustic image and the second photoacoustic image after the low pass filter processing.

13. The photoacoustic image evaluation apparatus according to claim 11,
wherein the processor extracts a region of a blood vessel having the preset thickness or less as the first blood vessel region and the second blood vessel region.

14. The photoacoustic image evaluation apparatus according to claim 13,
wherein the processor extracts a region of a blood vessel of 30 µm or more and 300 µm or less as the first blood vessel region and the second blood vessel region.

15. The photoacoustic image evaluation apparatus according to claim 2,
wherein the processor performs the registration processing by block matching and image deformation processing.

16. The photoacoustic image evaluation apparatus according to claim 2,
wherein the processor performs a plurality of emphasis processing using a plurality of Hessian filters corresponding to a plurality of blood vessel diameters on the first photoacoustic image and the second photoacoustic image, extracts the first blood vessel region by integrating blood vessel regions extracted from the first photoacoustic image after the plurality of emphasis processing, and extracts the second blood vessel region by integrating blood vessel regions extracted from the second photoacoustic image after the plurality of emphasis processing.

17. The photoacoustic image evaluation apparatus according to claim 2,
wherein the processor acquires a regenerated blood vessel region based on the first blood vessel region and the second blood vessel region and acquires the blood vessel regeneration index based on a pattern of a shape of the regenerated blood vessel region.

18. The photoacoustic image evaluation apparatus according to claim 17,
wherein the processor specifies, as the pattern of the shape of the regenerated blood vessel region, a pattern extending continuously over a preset length or more.

19. The photoacoustic image evaluation apparatus according to claim 17,
wherein processor specifies, as the pattern of the shape of the regenerated blood vessel region, a pattern in which a plurality of partial blood vessel regions having a preset length or less are intermittently distributed.

20. riginal) The photoacoustic image evaluation apparatus according to claim 2,
wherein the processor calculates, as the blood vessel regeneration index, a degree of increase of the number of pixels of the first blood vessel region with respect to the number of pixels of the second blood vessel region.

21. The photoacoustic image evaluation apparatus according to claim 2,
wherein the processor calculates, as the blood vessel regeneration index, a degree of increase of an area of the first blood vessel region with respect to an area of the second blood vessel region.

22. The photoacoustic image evaluation apparatus according to claim 1,
wherein the processor displays the first photoacoustic image and the second photoacoustic image side by side on the display.

23. The photoacoustic image evaluation apparatus according to claim 1,
wherein the first photoacoustic image and the second photoacoustic image are two-dimensional images.

24. The photoacoustic image evaluation apparatus according to claim 1, wherein the first photoacoustic image and the second photoacoustic image are three-dimensional images.

25. A photoacoustic image generation apparatus comprising:
a light guide plate that emits light to a subject subjected to blood vessel regeneration treatment:
a probe having a transducer array in which a plurality of transducers are arranged and that detects photoacoustic waves generated inside the subject by emission of light into the subject; and
a processor configured to:
generate a photoacoustic image based on the photoacoustic waves detected by the transducer array;
acquire a first photoacoustic image generated at a first point in time and a second photoacoustic image generated at a second point in time before the first point in time;
acquire a blood vessel regeneration index, which indicates a state of a blood vessel by the regeneration treatment, based on a difference between a blood vessel included in the first photoacoustic image and a blood vessel included in the second photoacoustic image; and
display the blood vessel regeneration index on a display.

26. The photoacoustic image generation apparatus according to claim 25,
wherein a wavelength of light emitted from the light guide plate is 500 nm or more and 1200 nm or less.

27. The photoacoustic image generation apparatus according to claim 25,
wherein a center frequency of the probe is 9 MHz or more and 50 MHz or less.

28. The photoacoustic image generation apparatus according to claim 25,
wherein a pitch between the transducers in the transducer array is 0.05 μm or more and 200 μm or less.

29. A photoacoustic, image evaluation method comprising:
acquiring a first photoacoustic image generated at a first point in time and a second photoacoustic image generated at a second point in time before the first point in time, the first and second photoacoustic images being photoacoustic images generated by detecting photoacoustic waves generated inside a subject, who has been subjected to blood vessel regeneration treatment, by emission of light into the subject;
acquiring a blood vessel regeneration index, which indicates a state of a blood vessel by the regeneration treatment, based on a difference between a blood vessel included in the first photoacoustic: image and a blood vessel included in the second photoacoustic image; and
displaying the blood vessel regeneration index on a display.

30. A non-transitory computer readable recording medium storing a photoacoustic image evaluation program causing a computer to:
acquire a first photoacoustic image generated at a first point in time and a second photoacoustic image generated at a second point in time before the first point in time, the first and second photoacoustic images being photoacoustic images generated by detecting photoacoustic waves generated inside a subject, who has been subjected to blood vessel regeneration treatment, by emission of light into the subject;
acquire a blood vessel regeneration index, which indicates a state of a blood vessel by the regeneration treatment, based on a difference between a blood vessel included in the first photoacoustic image and a blood vessel included in the second photoacoustic image; and
display the blood vessel regeneration index on a display.

* * * * *